(12) United States Patent
Ling et al.

(10) Patent No.: US 7,952,706 B2
(45) Date of Patent: May 31, 2011

(54) MULTI-CHANNEL FIBER OPTIC SPECTROSCOPY SYSTEMS EMPLOYING INTEGRATED OPTICS MODULES

(75) Inventors: Jian Ling, San Antonio, TX (US); Joseph N. Mitchell, San Antonio, TX (US); Michael E. Sullivan, Raleigh, NC (US); James F. Brennan, III, Matthews, NC (US); Mark R. Heistand, San Antonio, TX (US); Jon Nazemi, Cambridge, MA (US); William Fraker, Cave Creek, AZ (US)

(73) Assignee: Prescient Medical, Inc., Doylestown, PA (US)

( * ) Notice: Subject to any disclaimer, the term of this patent is extended or adjusted under 35 U.S.C. 154(b) by 80 days.

(21) Appl. No.: 12/122,678

(22) Filed: May 17, 2008

(65) Prior Publication Data

US 2009/0231578 A1    Sep. 17, 2009

Related U.S. Application Data

(60) Provisional application No. 60/924,497, filed on May 17, 2007.

(51) Int. Cl.
*G01J 3/44* (2006.01)
(52) U.S. Cl. ........................................ 356/301
(58) Field of Classification Search .................. 356/301
See application file for complete search history.

(56) References Cited

U.S. PATENT DOCUMENTS

| | | | |
|---|---|---|---|
| 5,764,823 A | 6/1998 | Shapanus et al. | |
| H2002 H * | 11/2001 | McLachlan et al. | ........... 356/301 |
| 6,353,476 B1 | 3/2002 | Allen et al. | |
| 6,522,913 B2 | 2/2003 | Panescu et al. | |
| 6,597,000 B2 | 7/2003 | Stern | |
| 6,615,063 B1 | 9/2003 | Ntziachristos et al. | |
| 6,675,106 B1 | 1/2004 | Keenan et al. | |
| 6,701,181 B2 | 3/2004 | Tang et al. | |
| 6,873,868 B2 | 3/2005 | Furnish | |
| 6,949,072 B2 | 9/2005 | Furnish et al. | |
| 7,039,452 B2 * | 5/2006 | McClane et al. | ............... 600/424 |
| 7,153,299 B1 | 12/2006 | Tu et al. | |
| 2002/0183622 A1 | 12/2002 | Zuluaga et al. | |
| 2003/0047608 A1 | 3/2003 | Huss et al. | |
| 2003/0125630 A1 | 7/2003 | Furnish | |
| 2004/0260182 A1 | 12/2004 | Zuluaga et al. | |
| 2005/0054934 A1 | 3/2005 | Furnish et al. | |
| 2005/0075574 A1 | 4/2005 | Furnish et al. | |
| 2005/0165315 A1 | 7/2005 | Zuluaga et al. | |
| 2006/0139633 A1 * | 6/2006 | Puppels et al. | ................. 356/301 |

FOREIGN PATENT DOCUMENTS

WO    WO-2007-032814 A2    3/2007

OTHER PUBLICATIONS

Utzinger et al., "Fiber Optical probes for Biomedical Optical Spectroscopy," *J. Biomed*, 2003: 8(1), pp. 121-147.

(Continued)

*Primary Examiner* — Tarifur Chowdhury
*Assistant Examiner* — Abdullahi Nur
(74) *Attorney, Agent, or Firm* — Patton Boggs LLP (57) ABSTRACT

The invention provides unitary optics modules that integrate several light management functions for performing optical spectroscopy, such as Raman spectroscopy, and optical spectroscopy systems that include one or more of the unitary optics modules. Methods of using the modules and systems are also provided.

17 Claims, 4 Drawing Sheets

OTHER PUBLICATIONS

Edwards et al., "Potential Applications of FT-Raman Spectroscopy for Dermatological Diagnostics," *J. Mol. Struc.*, 1995: 347, pp. 379-388.

International Search Report and Written Opinion for PCT/US08/64029, dated Sep. 4, 2008.

* cited by examiner

MULTI-CHANNEL FIBER OPTIC SPECTROSCOPY SYSTEMS EMPLOYING INTEGRATED OPTICS MODULES

This application claims the benefit of U.S. provisional application Ser. No. 60/924,497 filed May 17, 2007, which is incorporated by reference herein in its entirety.

FIELD OF THE INVENTION

The invention relates to the field of light management for Raman spectroscopy.

BACKGROUND OF INVENTION

Optical fibers permit delivery to and collection of light from otherwise inaccessible locations for optical analysis, for example, by Raman spectroscopy, Near Infra-Red absorbance spectroscopy, laser-induced fluorescence spectroscopy such as time-resolved laser-induced fluorescence spectroscopy (TR-LIFS).

U.S. Pat. No. 6,522,913 discloses systems and methods for visualizing tissue during diagnostic or therapeutic procedures that utilize a support structure that brings sensors into contact with the lumen wall of a blood vessel, and is incorporated by reference herein in its entirety U.S. Pat. No. 6,701,181 discloses multi-path optical catheters, and is incorporated by reference herein in its entirety.

U.S. Pat. No. 6,873,868 discloses multi-fiber catheter probe arrangements for tissue analysis or treatment, and is incorporated by reference herein in its entirety.

U.S. Pat. No. 6,949,072 discloses devices for vulnerable plaque detection, and is incorporated by reference herein in its entirety.

U.S. Publication No. 2002/0183622 discloses a fiber-optic apparatus and method for the optical imaging of tissue samples, and is incorporated by reference herein in its entirety.

U.S. Publication No. 2003/0125630 discloses catheter probe arrangements for tissue analysis by radiant energy delivery and radiant energy collection, and is incorporated by reference herein in its entirety.

U.S. Publication No. 2004/0260182 discloses intraluminal spectroscope devices with wall-contacting probes, and is incorporated by reference herein in its entirety.

U.S. Publication No. 2005/0054934 discloses an optical catheter with dual-stage beam redirector, and is incorporated by reference herein in its entirety.

U.S. Publication No. 2005/0075574 discloses devices for vulnerable plaque detection that utilize optical fiber temperature sensors, and is incorporated by reference herein in its entirety.

U.S. Publication No. 2005/0165315 discloses a side-firing fiber-optic array probe, and is incorporated by reference herein in its entirety.

U.S. Publication No. 2006/0139633 discloses the use of high wavenumber Raman spectroscopy for evaluating tissue, and is incorporated by reference herein in its entirety.

SUMMARY OF INVENTION

The invention provides unitary optics modules that integrate several light management functions for optical spectroscopy, such as Raman spectroscopy, Near Infra-Red absorbance spectroscopy, laser-induced fluorescence spectroscopy and time-resolved laser-induced fluorescence spectroscopy (TR-LIFS), and spectroscopy systems that include multiple optical channels each having an integrated optics module.

One embodiment of the invention provides an integrated optics module that includes:
- a dichroic beam splitter 101 selected to pass light of a wavelength for illumination of a sample and reflect light in a wavelength region of interest for analysis;
- a laser line filter 104 disposed to pass a narrow wavelength band of light toward and through the dichroic beam splitter illuminate a sample for analysis, and
- a long-pass edge filter 105 disposed to receive and pass light reflected by the dichroic beam splitter after returning from illuminating the sample.

The integrated optics module may be unitary, for example, in the form of a block or with components joined to or secured by a frame in their functional positions.

A related embodiment of the invention provides a multiple channel optical spectroscopy system that includes:
- a plurality of optical channels, wherein each of at least two of the plurality of optical channels includes:
   an integrated optics module including:
      a dichroic beam splitter 101 selected to pass light of a wavelength for illumination of a sample and reflect light in a wavelength region of interest for analysis;
      a laser line filter 104 disposed to pass a narrow wavelength band of light toward and through the dichroic beam splitter illuminate a sample for analysis, and
      a long-pass edge filter 105 disposed to receive and pass light reflected by the dichroic beam splitter after returning from illuminating the sample;
   a sample-side optical fiber connected on one end to the integrated optics module and adapted on the other end to connect to a multiple channel optical probe, such that laser light is deliverable to a sample via the sample side optical fiber and light collected from a sample is deliverable to the dichroic beam splitter via the sample side optical fiber,
   a light source-side optical fiber operably connectable to a light source on one end and connected to the integrated optics module at the other end, such that light from the light source is deliverable to pass through the laser line filter towards and through the dichroic beam splitter to illuminate a sample;
   a spectrometer-side optical fiber configured to deliver light collected from a sample by the sample side optical fiber and reflected by the dichroic beam splitter to a spectrometer;
- an optical spectrometer configured to simultaneously receive and separately measure optical signals from more than one spectrometer side optical fiber; and
- a laser light source configured to simultaneously launch light into multiple optical channels.

In one variation, the optical spectrometer is configured to spatially segregate optical signals received from multiple optical fibers defining different channels that are simultaneously measured. In another variation, the system further includes a multiple channel optical probe, wherein each channel includes an optical fiber and each channel has a different field of view. The multiple channel optical probe may, for example, be an intravascular catheter. The optical probe may, for example, be a basket catheter, such as an intravascular basket catheter. In one variation, the system may further include an optical switch configured to switch illumination from the light source between different sets of multiple light source-side optical fibers.

In another variation of the system, the integrated optics module further includes: a first collimator lens 107 disposed on the laser line filter of the optics module, said first collimator lens being configured to receive light from the laser via the light source-side optical fiber; a second collimator lens 109 disposed on the probe-side optical fiber of the optics module, said second collimator lens being configured to receive light launched by the light source-side optical fiber through the laser line filter which passes through the dichroic mirror and deliver said light to an optical fiber toward a sample and deliver light returned from the sample back into the integrated optics module; and a third collimator lens 111 disposed on the long-pass optical filter, said third collimator lens, said third collimator lens configured to receive light returning through the probe side optical fiber which is reflected by the dichroic beam splitter through the long-pass filter and deliver said light to the Raman spectrometer.

In still another variation, a photodiode may be disposed on the integrated optical module(s) such that it receives a portion of the laser light that is reflected by the dichroic beam splitter rather than passing through the dichroic beam splitter, in order to measure the intensity of light entering the channel(s) of the system from the light source.

In another variation, the system is configured to perform Raman spectroscopy, the dichroic beam splitter is selected to pass light of a wavelength for illumination of a sample and reflect Raman scattered light in a wavenumber region of interest; and the spectrometer is a Raman spectrometer configured to measure light in the wavenumber region of interest. The system may, for example, be configured to measure Raman scattered light in the wavenumber range of approximately 2,600 to 3,200 $cm^{-1}$.

In still another variation of the system, the integrated optics module further includes: a first collimator lens 107 disposed on the laser line filter of the optics module, said first collimator lens being configured to receive light from the light source via the light source-side optical fiber; a second collimator lens 109 disposed on the probe-side optical fiber of the optics module, said second collimator lens being configured to receive light launched by the light source-side optical fiber through the laser line filter which passes through the dichroic mirror and deliver said light to an optical fiber toward a sample and deliver light returned from the sample back into the integrated optics module; and a third collimator lens 111 disposed on the long-pass optical filter, said third collimator lens, said third collimator lens configured to receive light returning through the probe side optical fiber which is reflected by the dichroic beam splitter through the long-pass filter and deliver said light to the Raman spectrometer. A photodiode may be disposed on the integrated optical module such that it receives a portion of the laser light that is reflected by the dichroic beam splitter rather than passing through the dichroic beam splitter, in order to measure light intensity.

Another embodiment of the invention provides a method for evaluating a blood vessel, such as an artery, in order to determine the presence, absence and/or location of atherosclerotic lesions, such as lipid-rich lesions, such as vulnerable plaques, that includes the step of: providing an optical spectroscopy system, such as a Raman spectroscopy system, according to the invention, which may be a multi-fiber spectroscopy system; inserting an optical spectroscopy probe or optical catheter probe of the system into the lumen of a blood vessel; and optically interrogating the blood vessel wall by spectroscopy at one or more positions in the blood vessel using the system. In one Raman spectroscopy embodiment, the wavenumber region used for evaluating the blood vessel wall is in the range of approximately 2,600 to 3,200 $cm^{-1}$ (the "high wavenumber region") to, for example, evaluate the lipid content of the target. In another Raman spectroscopy embodiment, the wavenumber region used for evaluating the blood vessel wall is in the range of approximately 200 to 2,000 $cm^{-1}$ (the "fingerprint region"), such as in the range of approximately 800 to 1,200 $cm^{-1}$, to, for example, evaluate the calcification of the target. In still another variation, wavenumber regions in each of the high wavenumber region and the fingerprint region (such as in the range of approximately 800 to 1,200 $cm^{-1}$ for the fingerprint region) are used for analysis, for example, in order to evaluate both the lipid content and calcification of the examined target.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION

The inventors have recognized that it is advantageous and desirable to simultaneously monitor multiple points of a target tissue, such as an arterial wall, using optical spectroscopy for the diagnosis of health and disease, whilst minimizing the cost and complexity of the spectroscopic systems used for such analyses. Accordingly, what is now provided are compact, multi-channel fiber optic spectroscopy systems that utilize separate optical fiber channels, each having its own filter/optics module and associated with a unique field of view relative to the other channels, and a single spectrometer that simultaneously and distinctly measures signals received from different optical channels. In contrast to the present invention, it is believed that prior optical spectroscopy systems which included a linear array of fibers coupled to a spectrometer carried the same signal in each of the fibers.

The invention is further described below with reference to the appended figures.

Figure 1:
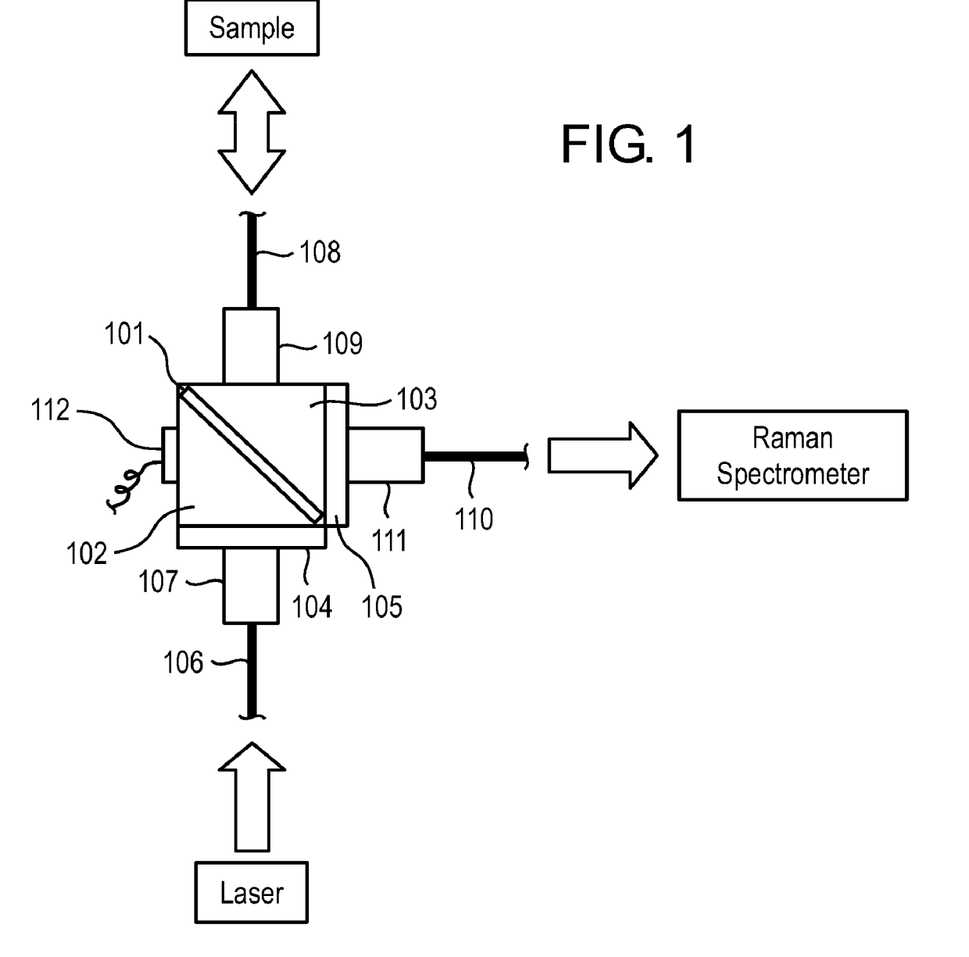
FIG. 1 shows an integrated optics module embodiment of the invention for Raman spectroscopy.

FIG. 1 shows an integrated optics module or "block" embodiment of the invention that includes several optical components for the implementation of Raman spectroscopy. A dichroic beam splitter 101, e.g., a dichroic mirror, is disposed between a first transparent triangular block 102 and a second transparent triangular block 103, each of said triangular blocks having three edges defining the triangular shape of the blocks. A laser line filter 104 is disposed on one outer edge of the first triangular block. This filter is selected to pass only a narrow wavelength band of light, which will be used to illuminate a sample/target for analysis. A long-pass edge filter 105 is disposed on an edge of the second triangular block that is adjacent to the edge of the first triangular block on which the laser line filter is disposed. The components of the optics module may be joined or affixed to each other by any means, for example, by an optics grade adhesive or by fitting into a stiff metallic frame. The integrated optics module may have a rectilinear profile, such as the square profile shown in the figure.

A laser-side optical fiber 106 is configured to launch laser light from a laser source through the laser line filter into the optical module. A collimator lens 107 may be disposed between the laser-side optical fiber and the laser line filter of the optics module. Collimator lenses used as described herein may, for example, be GRIN lenses.

A probe-side optical fiber 108 is configured to receive laser light launched by the laser-side optical fiber through the laser line filter which passes through the dichroic mirror and deliver said light to a sample/target and return light from the sample/target. A collimator lens 109 may be disposed between the probe-side optical fiber and the optics module.

A spectrometer-side optical fiber 110 in optical communication with the long-pass edge filter and configured to receive light returning through the probe side optical fiber which is reflected by the dichroic beam splitter through the long-pass filter and deliver said light to a spectrometer is provided. A collimator lens 111 may be disposed between the spectrometer side optical fiber and the long-pass optical filter.

The optical fibers may be joined to the integrated optics module in any suitable manner. For example, the optical fibers may each be joined with epoxy to a ferrule, which is then mounted in a tube in which the collimator lens is mounted, wherein the tube is alignedly mounted to or is part of the integrated optics module block.

A light measuring device 112 such as a photodiode may be disposed on the outer side of the first triangular block that is adjacent to the side on which the laser line filter is disposed.

The invention also provides an alternative yet analogous integrated optics module embodiment of the invention in which a frame, such as a cubicle frame, is provided that holds (or serves as the "platform" for mounting) the various components of the filter block. In this case, there are no transparent triangular blocks of the type described above for the embodiment of FIG. 1 and the frame may be essentially hollow with the dichroic mirror (beam splitter) mounted in its interior. Those skilled in the art will appreciate that a filter block according to the invention can be constructed in a variety of ways without departing from the spirit and scope of the invention.

The compact and efficient integrated optical module design of the invention is well suited to provide the light filtering and redirection functions associated with various types of optical spectroscopy, such as Raman spectroscopy, Near Infra-Red absorbance spectroscopy, laser-induced fluorescence spectroscopy and time-resolved laser-induced fluorescence spectroscopy (TR-LIFS). Those skilled in the art will appreciate that, irrespective of the type of optical spectroscopy, the laser side filter of an integrated optics system will be selected to pass only excitation light of a desired wavelength band, the beam splitter will be selected to pass the filtered excitation light and to reflect collected light of wavelengths of interest for analysis, and the spectrometer side filter will generally be a long-pass filter.

The invention is further exemplified below with respect to Raman spectroscopy embodiments.

In brief, the components illustrated in FIG. 1 function in the performance of Raman spectroscopy in the following manner. The laser side optical fiber 106 delivers the laser beam to a laser side collimator lens 107. The collimated laser beam then passes through a laser line filter 104 in the integrated optics module to ensure the spectral purity of the laser beam before projecting onto a dichroic beam splitter/mirror 101. The dichroic beam splitter transmits the majority of the laser beam into the sending/receiving fiber 108 through the sending/receiving collimator 109. Probe side optical fiber 108 may be connected to a fiber in a multiple-fiber probe (not shown), such a multi-fiber intravascular catheter, to deliver the laser beam to a target, and at the same time, to collect scattering light from the target.

The scattered light transmitted back from the target through probe-side optical fiber 108 is then projected onto the same dichroic beam splitter/mirror 101 after passing through the sample side collimator lens 109. The dichroic beam splitter is selected to at least predominantly transmit the emission wavelength of the laser but reflect Raman scattered light, as received back from a target, in a wavelength range of interest. Accordingly, beam splitter 101 then reflects the Raman signals received from the target toward spectrometer-side collimator lens 111 and spectrometer-side optical fiber 110. The beam splitter may also be selected to not reflect the Rayleigh scattered light arising from the probe-side optical fiber.

The Raman scattered light reflected by beam splitter 101 is incident upon the long-pass edge filter 105, which blocks the Rayleigh scattered light and only allows the Raman signals in a range of interest to passed into spectrometer side collimator lens 111 and then spectrometer-side optical fiber 110 to be delivered to a Raman spectrometer. Some residual Rayleigh scattered light will be reflected by the beam splitter and toward the spectrometer. Although this portion is very small, the Rayleigh light signal is many orders of magnitude greater than the Raman scattered light signal from the sample and thus the long pass filter may be used to clean up the signal sent to the spectrometer.

The Raman scattered light is coupled into the spectrometer-side optical fiber through the spectrometer side collimator. The Raman signal path through the module provides high efficiency coupling.

While the majority of the laser intensity from the laser light source is transmitted through the dichroic beam splitter (toward the target), a portion of the laser beam as launched is reflected by dichroic beam splitter, and projected onto the photodiode. The photodiode is used to monitor a small portion of laser beam that is linearly proportional to the laser beam delivered onto the target. Accordingly, a light measuring device such as a photodiode, after calibration, can be used to monitor the amount of laser power delivered to a target.

Figure 2:
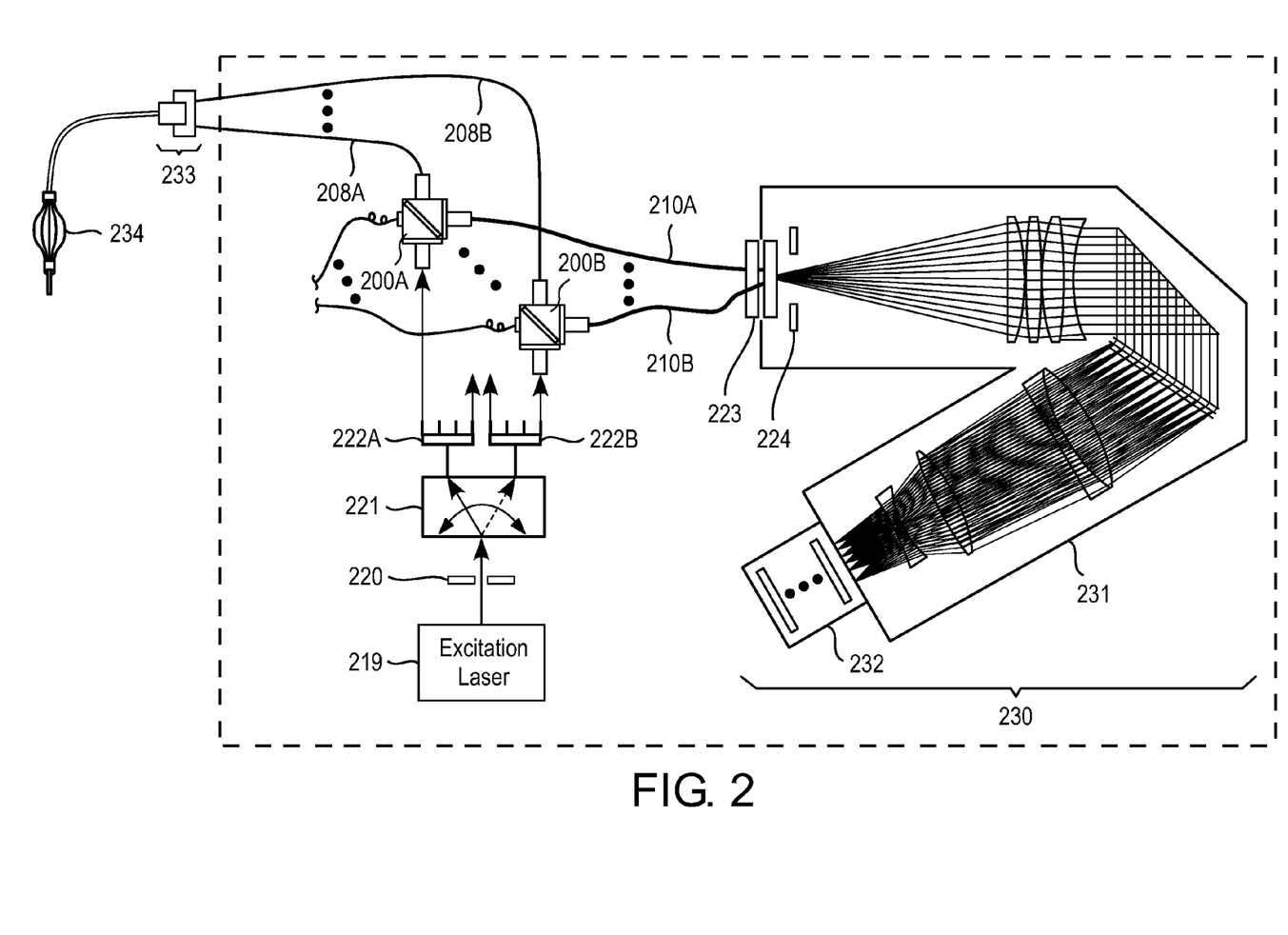
FIG. 2 shows an integrated Raman spectroscopy system embodiment of the invention.

The integrated optics modules and layout described above may advantageously be employed in providing a multi-optical fiber optical spectroscopy system, such as the Raman spectroscopy system exemplified in FIG. 2.

An excitation laser beam from a laser source 219, after passing through a laser-fiber coupler, is delivered into the input fiber on an optical fiber switch 221. A laser beam shutter 220 may be disposed between the laser and fiber coupler to control delivery (on/off) of the laser beam to the fiber. In the embodiment shown, the fiber switch connects to two 1×4 beam splitters, so that 4 optical fibers, i.e., channels, of eight total are illuminated at one time. Each dichroic beam splitter divides the laser source into multiple sub-sources that are combined together to form a sub-source group. The fiber switch controls the delivery of the laser beam to one of the two beam splitters at a time. Thus, only one group of sub-sources is turned on for data collection at a time. Other configurations are also within the scope of and provided by the invention such as a similar six total channels embodiment in which the switching between two groups of three channels is occurs.

Switching between smaller groups or individual channels is also within the scope of and provided by the invention. The invention also provides related embodiments in which there is no optical switch, but instead light is launched into all of the optical fibers at once using one or more beam splitters (as 222).

Figure 3:
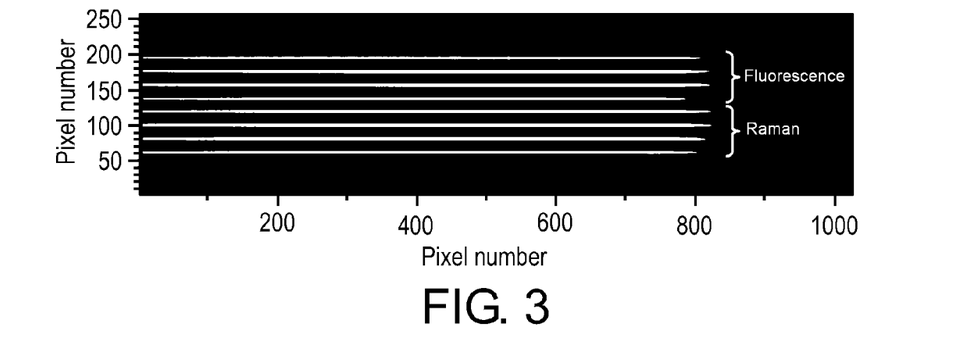
FIG. 3 shows an image captured by a CCD camera from a system embodiment of the invention having four Raman spectroscopy channels and four fluorescence spectroscopy channels.

FIG. 3 shows an image captured by a CCD camera from a system embodiment of the invention having four Raman spectroscopy channels and four fluorescence spectroscopy channels. The output of each optical fiber channel is at a separate vertical position, and for each channel the output is dispersed by wavelength along the horizontal axis.

Use of multiple laser sources is also within the scope of and provided by the invention. In this case a switch may be provided before beam splitter 222 to control which laser provides light into the system. A laser emitting at or around 671 nm may for example be used for high wavenumber Raman spectroscopy and a laser emitting at or around 830 nm may for example be used for fingerprint region Raman spectroscopy of biological tissues such as vasculature. Any suitable laser sources may be used including without limitation diode pumped solid state lasers (DPSS). Volume Bragg Grating (VBG) stabilized multi-mode laser diode sources, such as those available from PD-LD, Inc. (Pennington, N.J.) may also be used.

Each sub-source from a beam splitter is connected to a laser fiber of an integrated optics module 200A and B, as shown in FIG. 1. The laser beam is transmitted through the integrated optics module into the probe-side optical fibers, exemplified by 208A and B.

In the embodiment shown, multiple integrated optics modules are used to transmit multiple sub-sources from the beam splitters to different probe-side optical fibers with one integrated optics module per fiber sub-source.

The probe-side optical fibers connect to a multiple-fiber probe, such as a multi-fiber intravascular catheter 234, via a fiber connector 233, such as a MTP connector, to deliver the laser light to a target. Raman scattered light collected from a target by the probe-side optical fibers is transmitted back to corresponding integrated optics modules, where it is manipulated as previously described and directed into the spectrometer-side optical fibers, exemplified by 210A and B, with high efficiency for delivery to a Raman spectrometer 230. Raman spectrometer 230 may be formed from a VPH spectral separation unit and a CCD camera detector unit as exemplified in the figure.

In the embodiment shown in FIG. 2, the multiple spectrometer side optical fibers are aligned in a linear-array (side-by-side) at the entrance of Raman spectrometer 230. Spatially distinct imaging of multiple optical fiber channels within a single spectrometer is a common feature of systems according to the invention irrespective of the type of optical spectroscopy for which the system is configured. A slit 223 may be placed at the fiber entrance to control the spectral resolution of the spectrometer. A CCD shutter 224 may be provided to control the exposure time. The Raman scattered light is passed through a first imaging lens to expand the signal light into parallel beams. The parallel beams are projected onto a mirror to fold the beam, which permits reduced spectrometer size. The folded beams are further transmitted to a volume-phase holographic (VPH) grating, which diffracts the Raman scattered light into different wavelengths. The VPH grating has the characteristics of high transmission efficiency and reduced polarization-dependence versus other diffraction elements.

A second imaging lens focuses the diffracted Raman signals onto a CCD camera. Different wavelengths of the Raman scattered light form a spectrum on the CCD camera. Raman spectra from the multiple optical fibers in the linear array form multiple spectra on the CCD camera at different vertical (spatially separated) locations. The CCD camera measures the multiple spectra and sends the data to a computer for analysis. Those skilled in the art will appreciate that other types of Raman spectrometers, such as others known in the art, may also be employed.

The invention also provides embodiments utilizing more than one type of spectroscopy, such as laser-induced fluorescence spectroscopy in addition to Raman spectroscopy. In these embodiments, the system of the invention may be configured so that light sampled for the various types of spectroscopy is directed to spatially distinct or "dedicated" areas of the CCD array of the spectrometer for measurement.

Figure 4:
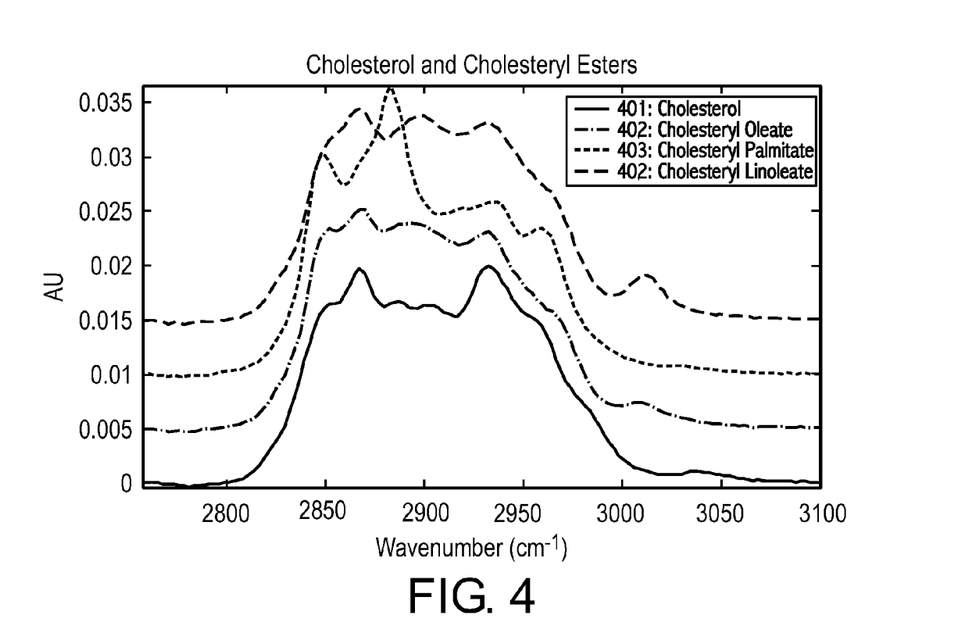
FIG. 4 shows Raman spectra of cholesterol and cholesterol esters.

In one embodiment, Raman spectroscopy systems according to the invention are configured to evaluate Raman scattered light in wavenumber regions associated with vascular health and disease states for the purposes of diagnosis and guiding treatment. FIG. 4 shows Raman spectra of cholesterol and cholesterol esters. Specifically, curve 401 is a Raman spectrum for cholesterol, curve 402 is a Raman spectrum for cholesteryl oleate, curve 403 is a Raman spectrum for cholesteryl palmitate and curve 404 is a Raman spectrum for cholesteryl linolenate.

Lipid components of lipid-rich atherosclerotic lesions, such as vulnerable plaques, have characteristic Raman spectra within the high wavenumber region, i.e., approximately 2,600 to 3,200 $cm^{-1}$. The so-called fingerprint region, i.e., 200 to 2,000 $cm^{-1}$ can also provide useful information. For example, atherosclerotic calcifications show a strong Raman signal at around 960 $cm^{-1}$. Hence, the apparatuses and systems of the invention are useful in locating and characterizing lipid-rich lesions, such as vulnerable plaques, in a blood vessel as well as locating and characterizing calcifying or calcified atherosclerotic lesions in a blood vessel and for distinguishing between lipid-rich and calcifying/calcified lesions in a blood vessel.

Figure 5:
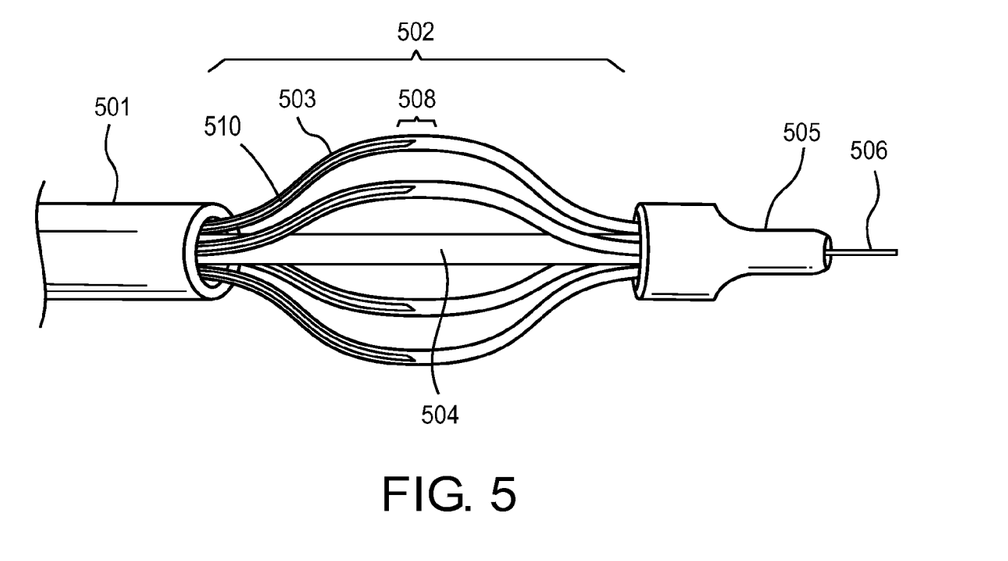
FIG. 5 shows a basket-style intravascular catheter that may be employed in a Raman spectroscopy system according the invention.

The present invention also provides optical spectroscopy systems, such as Raman spectroscopy systems, that include a side/lateral-viewing catheter in which optical components for interrogating the walls of blood vessel lumens are disposed on rods that can be flexed outward toward a blood vessel wall. FIG. 5 shows a basket-style side-viewing optical catheter embodiment of the invention that has a proximal outer shaft 501, a basket section 502 including four probe arms 503 each including one or more side viewing optical fiber assemblies 510, such as an end-angled optical fiber that terminates in or around the apex of the radially extended probe arm (side-viewing portion 508 of the basket section) in order to contact or near a vessel wall so that a Raman spectroscopic evaluation of the vessel wall can be performed. The catheter also includes a distal tip 505 that is connected to a guidewire tube 504, so that the catheter may travel over a guidewire 506, and to the distal end of each probe arm. The viewing portion of the probe arms may have a window to permit direct viewing by the side-viewing portions of the optical fiber or optical fiber assemblies. Alternatively, the entire probe arm or at least the side-viewing portion of the optical fiber assembly may be enclosed in a fluoropolymer, such as an amorphous fluoropolymer, such as Teflon AF 2400. Such materials enable use of a "windowless" probe arms for fingerprint and high wavenumber Raman spectroscopic applications since they are sufficiently transparent to both near infra-red excitation wavelengths and the resulting wavelengths within the fingerprint and high wavenumber regions and since have very small Raman signatures themselves in the fingerprint and high wavenumber regions. Any suitable enclosure material as described herein may be used. It has been found that amorphous fluoropolymers have a sufficient rigidity to be used as the main structural element of the rods (arms) of the basket catheter. However, if necessary, each probe arm may also include a structural support element such as spring wire or durable polymer rod (not shown) to support the enclosed fiber optic probe. Radial expansion and contraction of the probe arms of the basket section may be accomplished by contracting and extending the opposite ends of the probe arms, respectively. The guidewire tube, which is attached to the distal tip of the catheter, may for example, be slideable within the catheter thereby permitting said contracting and extending of the opposite ends of the probe with respect to each other, while the proximal ends of the probe arms remain fixed with respect to the proximal outer shaft. Alternatively, for example, a slideable sheath may be provided to control the radial extension of the basket section. Optional radiopaque marker bands may also be provided to aid in visualizing the catheter within a blood vessel.

One related system embodiment of the invention includes a catheter apparatus for optically interrogating a blood vessel wall, that includes: multiple optical probe rod elements (e.g., 2, 3, 4, 6, or 8) along a central shaft of the catheter and extendable radially outward toward a blood vessel wall from an unextended configuration closer to the longitudinal axis of the catheter and an expandable balloon collectively enclosing the multiple rod elements. The rod elements each include an optical assembly for transmitting and receiving light from the vessel wall lateral to the axis of the catheter while the rod-elements contact or are near the wall. Each of the optical assemblies is in optical communication with at least one optical fiber that is in communication with a light source for illuminating the vessel wall and/or a detector for detecting light received from the vessel wall. The optical assemblies of each rod element may be disposed at or around the middle of a rod element or at or around whatever part of a rod element tends to extend most radially outward. Relative motion of the distal ends and proximal ends of the rods may be used to radially flex the rods outward toward a lumen wall and to radially retract the rods toward the catheter axis.

Another system embodiment of the invention includes a catheter apparatus for optically interrogating a blood vessel wall that includes: (1) a rod element portion near the distal end of the catheter comprising multiple rod elements along a central shaft of the catheter and extendable radially outward toward a blood vessel wall from an unextended configuration closer to the longitudinal axis of the catheter, wherein the rod elements each include an optical assembly for transmitting and receiving light from the vessel wall lateral to the axis of the catheter while the rod-elements contact or are near the wall and wherein each of the optical assemblies is in optical communication with at least one optical fiber that is in communication with a light source for illuminating the vessel wall and/or a detector for detecting light received from the vessel wall; and (2) a tip portion of the catheter that extends from the distal end of the rod element portion to the distal end of the catheter, wherein a guidewire conduit or channel extends from within the central shaft of the rod element portion of the catheter distally through the tip portion of the catheter. The guidewire channel or conduit may, for example, open within the rod element portion of the catheter and at or near the distal end of the tip portion of the catheter.

Any suitable sort of side/lateral-viewing optical assembly (ies) may be used and numerous sorts of side viewing optics are known in the art. For example, a 45-deg (or other angle) mirror face or a prism can be used to laterally direct/redirect light from an optical fiber. Similarly, an optical fiber can be provided with an angularly faceted tip to direct and receive light that is off-axis with respect to the fiber.

In addition to side/laterally-viewing windowless fiber optic Raman probes, the present invention also provides end/front-viewing windowless Raman spectroscopic probe embodiments.

The systems and apparatuses of the invention may be used for any purpose or in any application.

One embodiment of the invention provides a method for evaluating the health of blood vessels, for example, by diagnosing, characterizing and/or locating one or more atherosclerotic lesions in a blood vessel, such as an artery, by using a multi-fiber optical spectroscopy system, such as a Raman spectroscopy system, as described herein to optically evaluate the properties of a vessel wall at one more locations along the vessel.

A related embodiment of the invention provides a method for diagnosing and/or locating one or more lipid-rich atherosclerotic lesions in a blood vessel, such as a coronary artery of a subject, using a multi-fiber optical spectroscopy system, such as a Raman spectroscopy system, as described herein, to optically evaluate the properties of a vessel wall at one more locations along the vessel.

Still another related embodiment of the invention provides a method for diagnosing and/or locating one or more vulnerable plaque lesions in a blood vessel, such as a coronary artery of a subject, using a multi-fiber optical spectroscopy system, such as a Raman spectroscopy system, as described herein, to optically evaluate the properties of a vessel wall at one more locations along the vessel.

In one variation of the Raman spectroscopy embodiments of the invention, the wavenumber range used to evaluate the blood vessels by Raman spectroscopy is within the range of approximately 2,600 to 3,200 $cm^{-1}$, i.e., in the high wavenumber region. As shown in FIG. 4, various lipid components typical of blood vessel walls and atherosclerotic lesions thereof may be detected and characterized by examining within this wavenumber range.

The systems described throughout this disclosure may include one or more computers, or computer processors generally, working in conjunction with computer accessible memory, for controlling the system and/or for analyzing information obtained by the system. Similarly, systems according to the invention may include whatever control and/or signal processing circuitry is required to operate the system. For example, shutter controllers may be provided to operate shutters. In addition, the system embodiments of the invention may include one or more output devices such as a display for presenting information obtained from, about or based on optical spectroscopic analyses. The method embodiments of the invention may include one or more steps of storing, displaying and/or otherwise presenting information obtained from, about or based on optical spectroscopic analyses using the system, including but not limited to diagnostic categories associated with the optical spectroscopic data obtained.

Each of the patents and other publications cited in this disclosure is incorporated by reference in its entirety.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A multiple channel optical spectroscopy system, comprising:
   a plurality of optical channels, wherein each of at least two of the plurality of optical channels collects optical signals from unique locations, wherein each of at least two of the plurality of optical channels comprises:
   an integrated optics module comprising:
      a dichroic beam splitter selected to pass light of a wavelength for illumination of a sample and reflect light in a wavelength region of interest for analysis;
      a laser line filter disposed to pass a narrow wavelength band of light toward and through the dichroic beam splitter illuminate a sample for analysis, and
      a long-pass edge filter disposed to receive and pass light reflected by the dichroic beam splitter after returning from illuminating the sample;
   a sample-side optical fiber connected on one end to the integrated optics module and adapted on the other end to connect to a multiple channel optical probe, such that laser light is deliverable to a sample via the sample side optical fiber and light collected from a sample is deliverable to the dichroic beam splitter via the sample side optical fiber,
   a light source-side optical fiber operably connectable to a light source on one end and connected to the integrated optics module at the other end, such that light from the light source is deliverable to pass through the laser line filter towards and through the dichroic beam splitter to illuminate a sample;
   a spectrometer-side optical fiber configured to deliver light collected from a sample by the sample side optical fiber and reflected by the dichroic beam splitter to a spectrometer;
   a single optical spectrometer configured to simultaneously receive and simultaneously separately measure optical spectra including a range of wavelengths from more than one spectrometer side optical fiber; and
   a laser light source configured to simultaneously launch light into multiple optical channels.

2. The system of claim 1, wherein the optical spectrometer is configured to spatially segregate optical signals received from multiple optical fibers defining different channels that are simultaneously measured.

3. The system of claim 1, further comprising a multiple channel optical probe, wherein each channel comprises an optical fiber and each channel has a different field of view.

4. The system of claim 3, wherein the multiple channel optical probe is an intravascular catheter.

5. The system of claim 4, wherein the intravascular catheter is a basket catheter.

6. The system of claim 1, further comprising an optical switch configured to switch illumination from the light source between different sets of multiple light source-side optical fibers.

7. The system of claim 1, further comprising a computer operably connected to the spectrometer and an output device operably connected to the computer.

8. The system of claim 7, wherein the output device comprises a display.

9. The system of claim 7, wherein the computer is configured to store data obtained from the spectrometer in computer readable memory and/or analyze data obtained from the spectrometer.

10. The system of claim 1, further comprising a frame to which the components of the integrated optics unit are mounted in their functional configurations.

11. The system of claim 1, wherein the components of the integrated optics system are mounted to each other in their functional configurations.

12. The system of claim 1, wherein the integrated optics module further comprises:
   a first collimator lens disposed on the laser line filter of the optics module, said first collimator lens being configured to receive light from the laser via the light source-side optical fiber;
   a second collimator lens disposed on the probe-side optical fiber of the optics module, said second collimator lens being configured to receive light launched by the light source-side optical fiber through the laser line filter which passes through the dichroic mirror and deliver said light to an optical fiber toward a sample and deliver light returned from the sample back into the integrated optics module; and
   a third collimator lens disposed on the long-pass optical filter, said third collimator lens, said third collimator lens configured to receive light returning through the probe side optical fiber which is reflected by the dichroic beam splitter through the long-pass filter and deliver said light to the Raman spectrometer.

13. The system of claim 1, further comprising a photodiode disposed on the integrated optical module such that it receives a portion of the laser light that is reflected by the dichroic beam splitter rather than passing through the dichroic beam splitter.

14. The system of claim 1, wherein the system is configured to perform Raman spectroscopy and wherein:
   the dichroic beam splitter is selected to pass light of a wavelength for illumination of a sample and reflect Raman scattered light in a wavenumber region of interest; and
   the spectrometer is a Raman spectrometer configured to measure light in the wavenumber region of interest.

15. The system of claim 14, wherein the system is configured to measure Raman scattered light in the wavenumber range of approximately 2,600 to 3,200 $cm^{-1}$.

16. The system of claim 15, wherein the integrated optics module further comprises:
   a first collimator lens disposed on the laser line filter of the optics module, said first collimator lens being configured to receive light from the light source via the light source-side optical fiber;
   a second collimator lens disposed on the probe-side optical fiber of the optics module, said second collimator lens being configured to receive light launched by the light source-side optical fiber through the laser line filter which passes through the dichroic mirror and deliver said light to an optical fiber toward a sample and deliver light returned from the sample back into the integrated optics module; and
   a third collimator lens disposed on the long-pass optical filter, said third collimator lens, said third collimator lens configured to receive light returning through the probe side optical fiber which is reflected by the dichroic beam splitter through the long-pass filter and deliver said light to the Raman spectrometer.

17. The system of claim 14, further comprising a photodiode disposed on the integrated optical module such that it receives a portion of the laser light that is reflected by the dichroic beam splitter rather than passing through the dichroic beam splitter.

* * * * *